US006411852B1

United States Patent
Danek et al.

(10) Patent No.: US 6,411,852 B1
(45) Date of Patent: *Jun. 25, 2002

(54) MODIFICATION OF AIRWAYS BY APPLICATION OF ENERGY

(75) Inventors: Christopher J. Danek, Palo Alto; Thomas M. Keast, San Jose; Bryan E. Loomas, Saratoga, all of CA (US)

(73) Assignee: Broncus Technologies, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/296,040

(22) Filed: Apr. 21, 1999

Related U.S. Application Data

(63) Continuation-in-part of application No. 09/095,323, filed on Jun. 10, 1998.

(51) Int. Cl.[7] .................................................. A61F 7/12
(52) U.S. Cl. ........................... 607/42; 607/89; 607/101; 607/96; 606/2; 606/14; 606/28; 606/41; 606/48; 606/50; 128/898
(58) Field of Search ............................ 607/88–94, 96, 607/98, 42, 101, 113; 128/898; 606/41, 48, 50

(56) References Cited

U.S. PATENT DOCUMENTS

| | | |
|---|---|---|
| 1,155,169 A | 9/1915 | Starkweather |
| 1,207,479 A | 12/1916 | Bisgaard |
| 2,072,346 A | 3/1937 | Smith |
| 3,568,659 A | 3/1971 | Karnegis |
| 3,692,029 A | 9/1972 | Adair |
| 4,522,212 A | 6/1985 | Gelinas et al. |

(List continued on next page.)

FOREIGN PATENT DOCUMENTS

| | | |
|---|---|---|
| EP | 0 908 150 A1 | 4/1999 |
| FR | 2659240 | 9/1991 |
| WO | WO 98/44854 A1 | 10/1998 |
| WO | WO 98/56324 A1 | 12/1998 |
| WO | WO 98/58681 A2 | 12/1998 |
| WO | WO 99/03413 A1 | 1/1999 |
| WO | WO 99/13779 A2 | 3/1999 |
| WO | WO 99/13779 A3 | 3/1999 |
| WO | WO 99/34741 A1 | 7/1999 |
| WO | WO 99/44506 A1 | 9/1999 |
| WO | WO 99/45855 A1 | 9/1999 |
| WO | WO 00/51510 A1 | 9/2000 |
| WO | WO 01/03642 A1 | 1/2001 |

OTHER PUBLICATIONS

Wiggs et al., "On the mechanism of mucosal folding in normal asthmatic airways", The American Physiological Society, 0161–7569/97, 1997.*

(List continued on next page.)

*Primary Examiner*—Linda C. M. Dvorak
*Assistant Examiner*—A. Farah
(74) *Attorney, Agent, or Firm*—Morrison & Foerster LLP

(57) ABSTRACT

A method for decreasing responsiveness or decreasing resistance to airflow of airways involves the transfer of energy to or from the airway walls to prevent or reduce airway constriction and other symptoms of lung diseases. The treatment reduces the ability of the airways to contract during an acute narrowing of the airways, reduces mucus plugging of the airways, and/or increases the airway diameter. The method provides a longer duration and/or more effective treatment for lung diseases than currently used drug treatments, and obviate patient compliance issues.

54 Claims, 10 Drawing Sheets

U.S. PATENT DOCUMENTS

| | | |
|---|---|---|
| 4,565,200 A | 1/1986 | Cosman |
| 4,584,998 A | 4/1986 | McGrail |
| 4,612,934 A * | 9/1986 | Borkan .................. 128/421 |
| 4,674,497 A | 6/1987 | Ogasawara |
| 4,706,688 A | 11/1987 | Michael et al. |
| 4,709,698 A | 12/1987 | Johnston et al. |
| 4,802,492 A | 2/1989 | Grunstein |
| 4,827,935 A * | 5/1989 | Geddes et al. ............. 128/419 |
| 4,862,886 A | 9/1989 | Clarke et al. |
| 4,920,978 A | 5/1990 | Colvin |
| 4,955,377 A | 9/1990 | Lennox et al. |
| 4,976,709 A | 12/1990 | Sand |
| 5,019,075 A | 5/1991 | Spears et al. |
| 5,053,033 A | 10/1991 | Clarke |
| 5,056,519 A * | 10/1991 | Vince .................... 128/419 |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,116,864 A | 5/1992 | March et al. |
| 5,117,828 A | 6/1992 | Metzger et al. |
| 5,135,517 A | 8/1992 | McCoy |
| 5,170,803 A | 12/1992 | Hewson et al. |
| 5,174,288 A | 12/1992 | Bardy et al. |
| 5,191,883 A | 3/1993 | Lennox et al. |
| 5,255,678 A | 10/1993 | Deslauriers et al. |
| 5,255,679 A | 10/1993 | Imran |
| 5,265,604 A * | 11/1993 | Vince .................... 607/42 |
| 5,281,218 A | 1/1994 | Imran |
| 5,293,869 A | 3/1994 | Edwards et al. |
| 5,309,910 A | 5/1994 | Edwards et al. |
| 5,313,943 A | 5/1994 | Houser et al. |
| 5,345,936 A | 9/1994 | Pomeranz et al. |
| 5,368,591 A | 11/1994 | Lennox et al. |
| 5,370,679 A | 12/1994 | Atlee, III |
| 5,374,287 A | 12/1994 | Rubin |
| 5,383,917 A | 1/1995 | Desai et al. |
| 5,394,880 A | 3/1995 | Atlee, III |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,423,744 A | 6/1995 | Gencheff et al. |
| 5,423,811 A | 6/1995 | Imran et al. |
| 5,431,696 A | 7/1995 | Atlee, III |
| 5,433,730 A | 7/1995 | Alt |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,496,311 A | 3/1996 | Abele et al. |
| 5,500,011 A | 3/1996 | Desai |
| 5,505,728 A * | 4/1996 | Ellman et al. ............. 606/39 |
| 5,509,419 A | 4/1996 | Edwards et al. |
| 5,522,862 A | 6/1996 | Testerman et al. |
| 5,531,779 A | 7/1996 | Dahl et al. |
| 5,545,161 A | 8/1996 | Imran |
| 5,545,193 A | 8/1996 | Fleischman et al. |
| 5,549,559 A | 8/1996 | Eshel |
| 5,549,655 A * | 8/1996 | Erickson .................. 607/42 |
| 5,558,073 A | 9/1996 | Pomeranz et al. |
| 5,562,608 A | 10/1996 | Sekins et al. |
| 5,588,432 A | 12/1996 | Crowley |
| 5,595,183 A | 1/1997 | Swanson et al. |
| 5,598,848 A | 2/1997 | Swanson et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,624,439 A * | 4/1997 | Edwards et al. ............. 606/45 |
| 5,626,618 A | 5/1997 | Ward et al. |
| 5,630,425 A | 5/1997 | Panescu et al. |
| 5,634,471 A * | 6/1997 | Fairfax et al. ............. 128/725 |
| 5,678,535 A * | 10/1997 | DiMarco ............... 128/200.24 |
| 5,680,860 A | 10/1997 | Imran |
| 5,681,308 A | 10/1997 | Edwards et al. |
| 5,693,078 A | 12/1997 | Desai et al. |
| 5,699,799 A * | 12/1997 | Xu et al. ................ 128/653.1 |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,730,128 A | 3/1998 | Pomeranz et al. |
| 5,730,726 A | 3/1998 | Klingenstein |
| 5,730,741 A | 3/1998 | Horzewski et al. |
| 5,740,808 A | 4/1998 | Panescu et al. |
| 5,752,518 A | 5/1998 | McGee et al. |
| 5,755,753 A | 5/1998 | Knowlton |
| 5,759,158 A | 6/1998 | Swanson |
| 5,769,846 A | 6/1998 | Edwards et al. |
| 5,772,590 A | 6/1998 | Webster, Jr. |
| 5,779,698 A | 7/1998 | Clayman et al. |
| 5,782,239 A | 7/1998 | Webster, Jr. |
| 5,782,899 A | 7/1998 | Imran |
| 5,792,064 A | 8/1998 | Panescu et al. |
| 5,795,303 A | 8/1998 | Swanson et al. |
| 5,807,306 A | 9/1998 | Shapland et al. |
| 5,810,807 A | 9/1998 | Ganz et al. |
| 5,827,277 A | 10/1998 | Edwards |
| 5,836,947 A | 11/1998 | Fleischman et al. |
| 5,843,075 A | 12/1998 | Taylor |
| 5,846,238 A | 12/1998 | Jackson et al. |
| 5,848,969 A | 12/1998 | Panescu et al. |
| 5,848,972 A | 12/1998 | Triedman et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,865 A | 2/1999 | Horzewski et al. |
| 5,881,727 A | 3/1999 | Edwards |
| 5,882,346 A | 3/1999 | Pomeranz et al. |
| 5,891,136 A | 4/1999 | McGee et al. |
| 5,897,554 A | 4/1999 | Chia et al. |
| 5,904,651 A | 5/1999 | Swanson et al. |
| 5,904,711 A | 5/1999 | Flom et al. |
| 5,908,445 A | 6/1999 | Whayne et al. |
| 5,908,446 A | 6/1999 | Imran |
| 5,911,218 A * | 6/1999 | DiMarco ............... 128/200.24 |
| 5,935,079 A | 8/1999 | Swanson et al. |
| 5,941,869 A | 8/1999 | Patterson et al. |
| 5,954,661 A | 9/1999 | Greenspon et al. |
| 5,954,662 A | 9/1999 | Swanson et al. |
| 5,964,753 A | 10/1999 | Edwards |
| 5,964,796 A | 10/1999 | Imran |
| 5,971,983 A | 10/1999 | Lesh |
| 5,972,026 A * | 10/1999 | Laufer et al. ............. 607/96 |
| 5,979,456 A * | 11/1999 | Magovern ............... 128/899 |
| 5,991,650 A | 11/1999 | Swanson et al. |
| 5,992,419 A | 11/1999 | Sterzer et al. |
| 5,993,462 A | 11/1999 | Pomeranz et al. |
| 5,999,855 A | 12/1999 | DiMarco |
| 6,004,269 A | 12/1999 | Crowley et al. |

| | | |
|---|---|---|
| 6,009,877 A | 1/2000 | Edwards |
| 6,024,740 A | 2/2000 | Lesh et al. |
| 6,036,687 A | 3/2000 | Laufer et al. |
| 6,053,172 A * | 4/2000 | Hovda et al. ............... 128/898 |
| 6,083,255 A | 7/2000 | Laufer et al. |
| 6,142,993 A | 11/2000 | Whayne et al. |
| 6,200,333 B1 | 3/2001 | Laufer |
| 6,254,598 B1 | 7/2001 | Edwards et al. |

OTHER PUBLICATIONS

U.S. application No. 09/176,899, Laufer, filed Oct. 22, 1998.

U.S. application No. 09/244,173, Laufer et al., filed Feb. 4, 1999.

U.S. application No. 09/280,672, Laufer et al., filed Mar. 29, 1999.

Barry R. Wiggs, et al., "On the Mechanism of Mucosal Folding in Normal and Asthmatic Airways," The American Physiological Society (1997) pp. 18141821.

Simon R. Johnson, et al. "Synthetic Functions of Airway Smooth Muscle in Asthma," Review.

P.T. Macklem, "Mechanical Factors Determining Maximum Bronchoconstriction," European Respiratory Journal, Supplemental 6 (1989) pp. 516s–519s.

James C. Hogg, "The Pathology of Asthma," APMIS, No. 105 (1997) pp. 735–745.

Dierkesmann et al. (1990). "Indication and Results of Endobronchial Laser Therapy," Lung (Suppl.):1095–1102.

Netter, F.H. (1979). "Respiratory System: A Compilation of Paintings Depicting Anatomy and Embryology, Physiology, Pathology, Pathophysiology, and Clinical Features and Treatment of Diseases," vol. 7 In The CIBA Collection of Medical Illustrations. M.B. Divertie, ed., Summit: New Jersey, pp. 119–135.

* cited by examiner

MODIFICATION OF AIRWAYS BY APPLICATION OF ENERGY

This is a Continuation-in-part application of U.S. application Ser. No. 09/095,323 filed Jun. 10, 1998, which is incorporated herein by reference in its entirety.

BACKGROUND OF THE INVENTION

1. Field of the Invention

The invention relates to a method for treating lung disease, and more particularly, the invention relates to a method for treating the lungs by applying energy to the airways to reduce the ability of the airways to constrict or to reduce the resistance to airflow through the airways.

2. Brief Description of the Related Art

Asthma is a disease in which (1) bronchoconstriction, (2) excessive mucus production, and (3) inflammation and swelling of airways occur, causing widespread but variable airflow obstruction thereby making it difficult for the asthma sufferer to breath. Asthma is a chronic disorder, primarily characterized by persistent airway inflammation. However, asthma is further characterized by acute episodes of additional airway narrowing via constriction of hyperresponsive airway smooth muscle.

Asthma stimuli may be allergenic or non-allergenic. Examples of allergenic stimuli include pollen, pet dander, dust mites, bacterial or viral infection, mold, dust, or airborne pollutants; non-allergenic stimuli include exercise or exposure to cold, dry air.

In asthma, chronic inflammatory processes in the airway play a central role. Many cells and cellular elements are involved in the inflammatory process, particularly mast cells, eosinophils T lymphocytes, neutrophils, epithelial cells, and even airway smooth muscle itself. The reactions of these cells result in an associated increase in the existing sensitivity and hyperresponsiveness of the airway smooth muscle cells that line the airways to the particular stimuli involved.

The chronic nature of asthma can also lead to remodeling of the airway wall (i.e., structural changes such as thickening or edema) which can further affect the function of the airway wall and influence airway hyperresponsiveness. Other physiologic changes associated with asthma include excess mucus production, and if the asthma is severe, mucus plugging, as well as ongoing epithelial denudation and repair. Epithelial denudation exposes the underlying tissue to substances that would not normally come in contact with them, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

Stimulus avoidance is accomplished via systematic identification and minimization of contact with each type of stimuli. It may, however, be impractical and not always helpful to avoid all potential stimuli.

Asthma is managed pharmacologically by: (1) long term control through use of anti-inflammatories and long-acting bronchodilators and (2) short term management of acute exacerbations through use of short-acting bronchodilators. Both approaches require repeated and regular use of the prescribed drugs. High doses of corticosteroid antiinflammatory drugs can have serious side effects that require careful management. In addition, some patients are resistant to steroid treatment. Patient compliance with pharmacologic management and stimulus avoidance is often a barrier to successful asthma management.

Asthma is a serious disease with growing numbers of suffers. Current management techniques are neither completely successful nor free from side effects.

Accordingly, it would be desirable to provide an asthma treatment which improves airflow without the need for patient compliance.

In addition to the airways of the lungs, other body conduits such as the esophagus, ureter, urethra, and coronary arteries, are also subject to periodic spasms which cause hypertrophy and hyperplasia of the smooth muscle around these body conduits reducing the inner diameter of the conduits.

SUMMARY OF THE INVENTION

The present invention relates to a method for treating bodily conduits by transfer of energy to or from the conduit walls to prevent the conduit from being able to constrict, to enlarge the conduit, or to reduce resistance to flow through the conduit. The invention is particularly directed to the treatment of the airways in the lungs to reduce the effects of asthma and other lung disease.

The present invention provides methods to decrease airway responsiveness and airway resistance to flow which may augment or replace current management techniques.

In accordance with one aspect of the present invention, a method for treating conditions of the lungs by decreasing airway responsiveness includes transferring energy to or from an airway wall to alter the airway wall in such a manner that the responsiveness of the airway is reduced.

In accordance with an additional aspect of the present invention, the energy transferred to or from the airway wall alters the structure of the airway wall.

In accordance with a further aspect of the present invention, the energy transferred to or from the airway wall alters the function of the airway wall.

In accordance with another aspect of the present invention, a method for treating conditions of the lungs by decreasing airway resistance to airflow includes transferring energy to or from an airway wall to alter the airway wall in such a manner that a resistance to airflow of the airway is decreased.

The present invention provides advantages of a treatment for asthma or other constriction or spasm of a bodily conduit by application of energy. The treatment reduces the ability of the airway to contract, reduces plugging of the airway, and/or increases the inner airway diameter.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
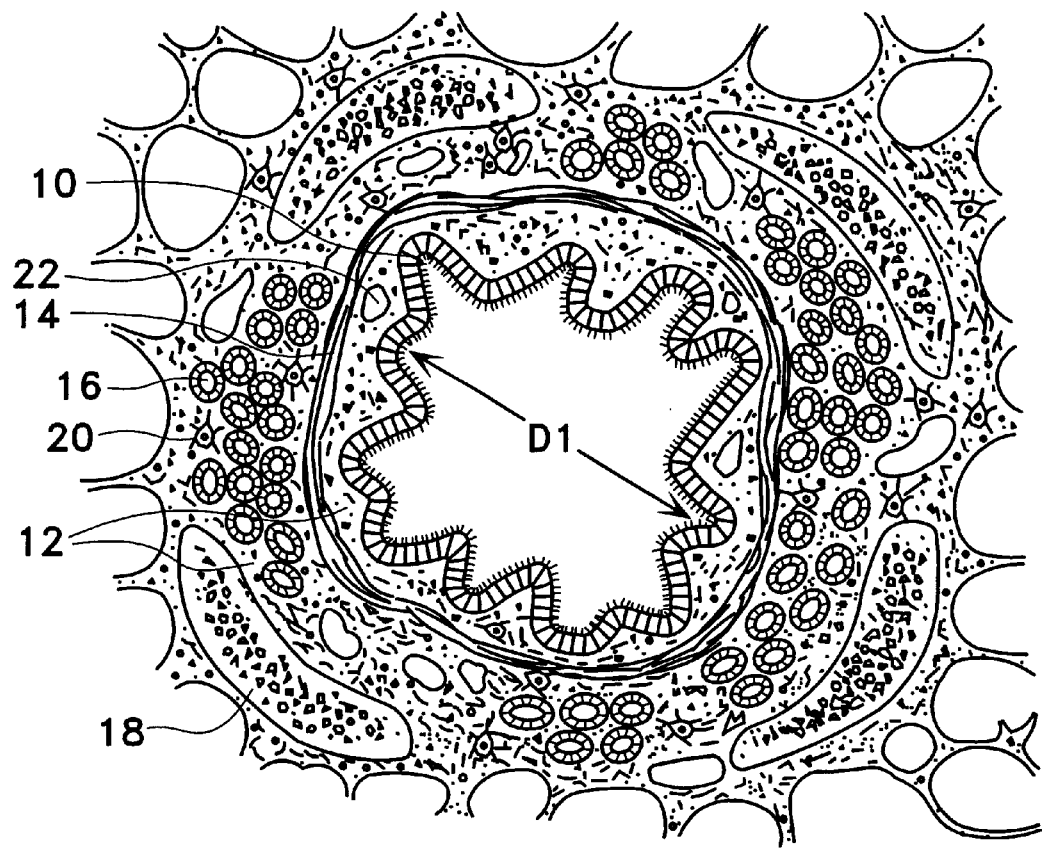
FIG. 1 is a cross sectional view of a medium sized bronchus in a healthy patient.
Figure 2:
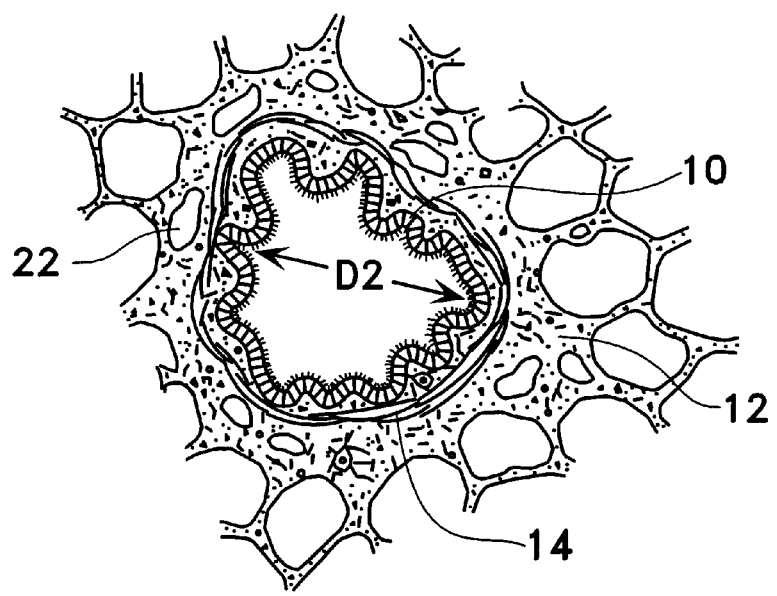
FIG. 2 is a cross sectional view of a bronchiole in a healthy patient.

FIGS. 1 and 2 illustrate cross sections of two different airways in a healthy patient. The airway of FIG. 1 is a medium sized bronchus having an airway diameter D1 of about 3 mm. FIG. 2 shows a section through a bronchiole having an airway diameter D2 of about 1.5 mm. Each airway includes a folded inner surface or epithelium 10 surrounded by stroma 12 and smooth muscle tissue 14. The larger airways including the bronchus shown in FIG. 1 also have mucous glands 16 and cartilage 18 surrounding the smooth muscle tissue 14. Nerve fibers 20 and blood vessels 22 also surround the airway.

Figure 3:
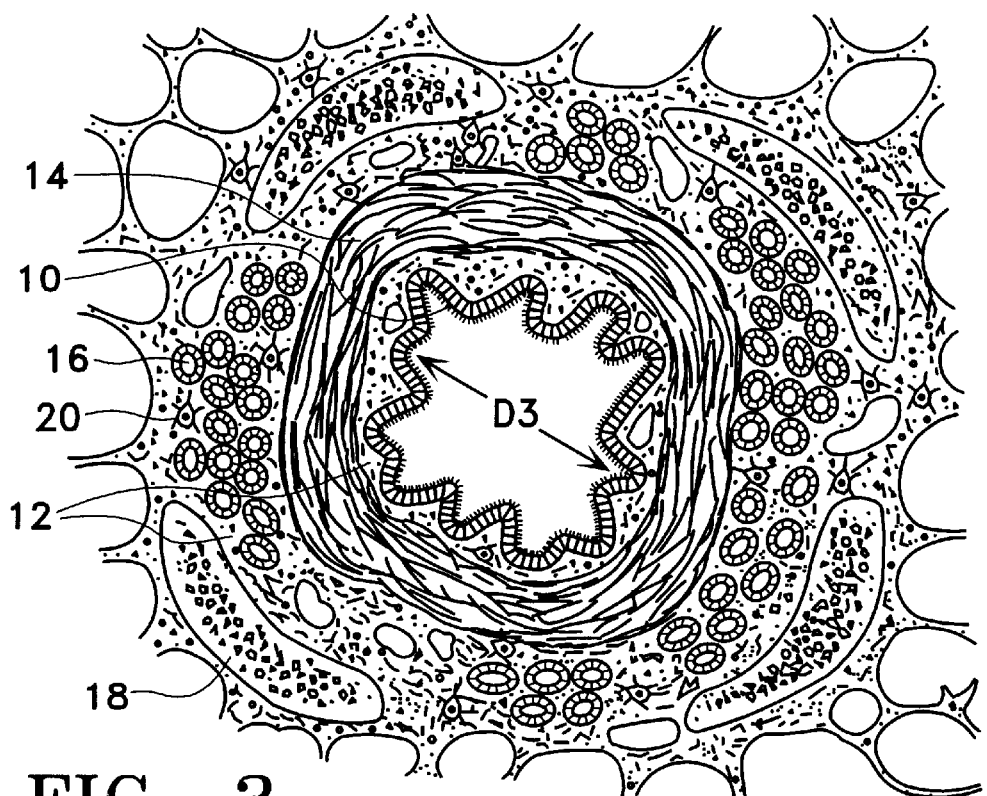
FIG. 3 is a cross sectional view of the bronchus of FIG. 1 showing the constriction occurring in an asthma patient.

FIG. 3 illustrates the bronchus of FIG. 1 in which the smooth muscle 14 has hypertrophied and increased in thickness causing the airway diameter to be reduced from the diameter D1 to a diameter D3.

There are several ways to decrease the resistance to airflow though the airways which occurs in asthma patients both at rest and during an asthma attack. One such treatment alters the structure of the airway, such as by reducing smooth muscle or other tissue. Another treatment alters the function of the airway, such as by reducing smooth muscle contraction, mucus gland secretions, or disrupting the inflammatory response. These treatments can be performed by applying energy of different types and in different patterns to achieve the desired results.

Figure 4:
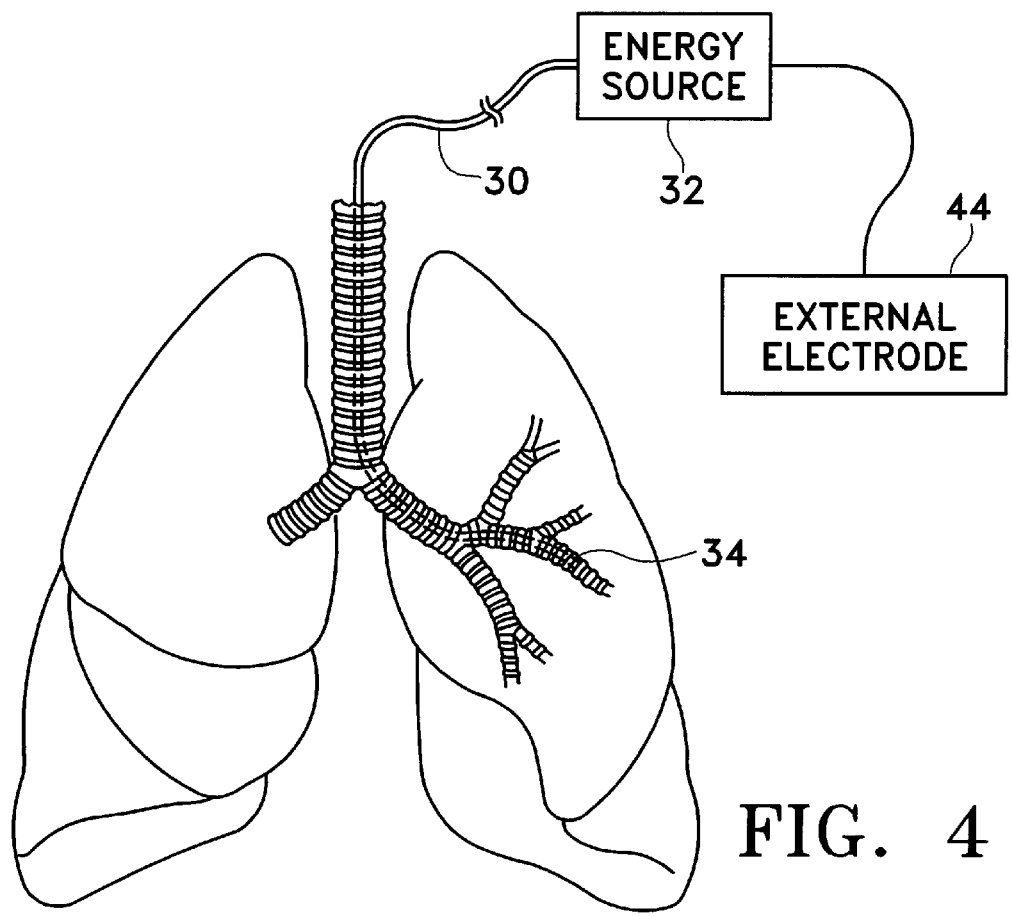
FIG. 4 is a schematic side view of the lungs being treated with a treatment device according to the present invention.

FIG. 4 is a schematic side view of the lungs being treated with a treatment device 30 according to the present invention. The treatment device 30 is an elongated member for delivery of energy from an energy source 32 to a treatment site 34 within the lungs. The energy may be delivered by the treatment device 30 in a variety of treatment patterns to achieve a desired response. Examples of patterns are discussed in further detail below. The energy which is delivered by the treatment device 30 may be any of a variety of types of energy including, but not limited to, radiant, laser, radio frequency, microwave, heat energy, or mechanical energy (such as in the form of cutting or mechanical dilation). In addition, the delivery of laser or light energy may be in conjunction with the delivery of a photodynamic agent, where the laser or light energy stimulates the photodynamic agent and initiates a cytotoxic, or cell damaging chemical reaction.

Reducing the Ability of the Airway to Contract

The energy treatment of the airways may be used to reduce the ability of the airways to narrow or reduce in caliber as a result of airway smooth muscle contraction. This treatment to reduce the ability of the smooth muscle to contract provides the benefit of lessening the severity of an asthma attack. The reduction in the ability of smooth muscle to contract may be achieved by treating the smooth muscle itself or by treating other tissues which in turn influence smooth muscle contraction or the response of the airway to smooth muscle contraction. Treatment may also reduce airway responsiveness or the tendency of the airway to narrow or constrict in response to stimulus.

The amount of smooth muscle surrounding the airway can be reduced by exposing the smooth muscle to energy which either kills the smooth muscle cells or prevents the cells from replicating. The reduction in smooth muscle reduces the ability of the smooth muscle to contract and narrow the airway during a spasm. The reduction in smooth muscle has the added benefit of increasing the caliber of the airways, reducing the resistance to airflow through the airways. In addition to use in debulking enlarged smooth muscle tissue to open up the airways, the method of the present invention may also be used for eliminating smooth muscle altogether. The elimination of the smooth muscle tissue prevents the hyperreactive airways of an asthma patient from contracting or spasming, reducing or eliminating this asthma symptom.

The ability of the smooth muscle to contract can also be altered by treatment of the smooth muscle in particular patterns. The smooth muscle is arranged around the airways in a generally helical pattern with pitch angles ranging from about −30 to about +30 degrees. Thus, the treatment of the smooth muscle by energy which is selectively delivered in an appropriate pattern can interrupt or cut through the helical pattern at a proper frequency and prevent the smooth muscle from constricting. This procedure of patterned application of energy eliminates contraction of the airways without completely eradicating smooth muscle. A pattern for treatment can be chosen from a variety of patterns including longitudinal stripes, circumferential bands, helical stripes, and the like as well as spot patterns having rectangular, elliptical, circular or other shapes. The size, number, and spacing of the treatment bands, stripes, or spots are chosen to provide a desired clinical effect of reduced airway responsiveness while limiting insult to the airway to a clinically acceptable level.

The patterned treatment of the tissues surrounding the airways with energy provides various advantages. The careful selection of the portion of the airway to be treated allows desired results to be achieved while the total healing load may be reduced. Patterned treatment can also achieve desired results with decreased morbidity, preservation of epithelium, and preservation of a continuous or near continuous ciliated inner surface of the airway for mucociliary clearance. The pattern of treatment may also be chosen to achieve desired results while limiting total treatment area and/or the number of airways treated, thereby improving speed and ease of treatment.

Application of energy to the smooth muscle surrounding the airways also may be used to cause the DNA of the smooth muscle cells to become cross linked. The treated smooth muscle cells with cross linked DNA are incapable of replicating. Accordingly, over time, as the smooth muscle cells die, the total thickness of smooth muscle decreases because of the inability of the cells to replicate. The programed cell death causing a reduction in the volume of tissue is called apoptosis. This treatment does not cause an immediate effect but causes shrinking of the smooth muscle and opening of the airway over time and substantially prevents regrowth. The application of energy to the walls of the airway also can be used to cause a cross linking of the DNA of the mucus gland cells preventing them from replicating and reducing excess mucus plugging or production over time.

The ability of the airways to contract can also be reduced by altering mechanical properties of the airway wall, such as by increasing stiffness of the wall or by increasing parenchymal tethering of the airway wall. Both of these methods provide increased forces which oppose contraction of the smooth muscle and narrowing of the airway.

There are several ways to increase the stiffness of the airway wall. One way to increase stiffness is to induce a fibrosis or wound healing response by causing trauma to the airway wall. The trauma can be caused by delivery of therapeutic energy to the tissue in the airway wall or by mechanical insult to the tissue. The energy is preferably delivered in such a way that it minimizes or limits the intra-luminal thickening that can occur.

Another way to increase the effective stiffness of the airway wall is by altering the submucosal folding of the airway upon narrowing. The submucosal layer is directly beneath the epithelium and its basement membrane and inside the airway smooth muscle. As an airway narrows, its perimeter remains relatively constant, with the mucosal layer folding upon itself. As the airway narrows further, the mucosal folds mechanically interfere with each other, effectively stiffening the airway. In asthmatic patients, the number of folds is fewer and the size of the folds is larger, and thus, the airway is free to narrow with less mechanical interference of mucosal folds than in a healthy patient. Thus, asthmatic patients have a decrease in stiffness of the airway and less resistance to narrowing.

The mucosal folding in asthmatic patients can be improved by treatment of the airway in a manner which encourages folding. Preferably, a treatment will increase the number of folds and/or decrease the size of the folds in the mucosal layer. For example, treatment of the airway wall in a pattern such as longitudinal stripes can encourage greater number of mucosal folds and increase airway stiffness.

The mucosal folding can also be increased by encouraging a greater number of smaller folds by reducing the thickness of the submucosal layer. The decreased thickness of the submucosal layer may be achieved by application of energy which either reduces the number of cells in the submucosal layer or which prevents replication of the cells in the submucosal layer. A thinner submucosal layer will have an increased tendency to fold and increased mechanical stiffening caused by the folds.

Another method for reducing the ability of the airways to contract is to improve parenchymal tethering. The parenchyma surrounds all airways and includes the alveolus and tissue connected to and surrounding the outer portion of the airway wall. The parenchyma includes the alveolus and tissue connected to and surrounding the cartilage that supports the larger airways. In a healthy patient, the parenchyma provides a tissue network which connects to and helps to support the airway. Edema or accumulation of fluid in lung tissue in asthmatic patients is believed to decouple the airway from the parenchyma reducing the restraining force of the parenchyma which opposes airway constriction. Application of therapeutic energy can be used to treat the parenchyma to reduce edema and/or improve parenchymal tethering.

In addition, energy can be used to improve connection between the airway smooth muscle and submucosal layer to the surrounding cartilage, and to encourage wound healing, collagen deposition, and/or fibrosis in the tissue surrounding the airway to help support the airway and prevent airway contraction.

Increasing the Airway Diameter

Airway diameter in asthmatic patients is reduced due to hypertrophy of the smooth muscle, chronic inflammation of the airway tissues, and general thickening of all parts of the airway wall. The overall airway diameter can be increased by a variety of techniques to improve the passage of air through the airways. Application of energy to the airway smooth muscle of an asthmatic patient can be used to debulk or reduce the volume of smooth muscle. This reduced volume of smooth muscle increases the airway diameter for improved air exchange.

The airway diameter can also be increased by reducing inflammation and edema of the tissue surrounding the airway. Inflammation and edema (accumulation of fluid) of the airway occur in an asthmatic patient due to irritation. The inflammation and edema can be reduced by application of energy to stimulate wound healing and regenerate normal tissue. Healing of the epithelium or sections of the epithelium experiencing ongoing denudation and renewal allows regeneration of healthy epithelium with less associated airway inflammation. The less inflamed airway has an increased airway diameter both at a resting state and in constriction. The wound healing can also deposit collagen which improves parachymal tethering.

Inflammatory mediators released by tissue in the airway wall may serve as a stimulus for airway smooth muscle contraction. Smooth muscle contraction, inflammation, and edema can be reduced by a therapy which reduces the production and release of inflammatory mediators. Examples of inflammatory mediators are cytokines, chemokines, and histamine. The tissues which produce and release inflammatory mediators include airway smooth muscle, epithelium, and mast cells. Treatment of these structures with energy can reduce the ability of the airway structures to produce or release inflammatory mediators.

The reduction in released inflammatory mediators will reduce chronic inflammation, thereby increasing the airway inner diameter, and may also reduce contraction of airway smooth muscle.

A further method for increasing the airway diameter is by denervation. A resting tone of smooth muscle is nerve regulated by release of catecholamines. Thus, by damaging or eliminating nerve tissue in the airways the resting tone of the airway smooth muscle will be reduced, and the airway diameter will be increased.

Reducing Plugging of the Airway

Excess mucus production and mucus plugging are common problems during both acute asthma exasterbations and in chronic asthma management. Excess mucus in the airways increases the resistance to airflow through the airways by physically blocking all or part of the airway. Excess mucus may also contribute to increased numbers of leukocytes found in airways of asthmatic patients by trapping leukocytes. Thus, excess mucus can increase chronic inflammation of the airways.

One type of asthma therapy involves treatment of the airways with energy to target and reduce mucus producing cells and glands. The treatment can eliminate all or a portion of the mucus producing cells and glands, can prevent the cells from replicating or can inhibit their ability to secrete mucus. This treatment will have both chronic benefits in increasing airflow through the airways and will lessen the severity of acute exacerbations.

FIGS. 5–19 illustrate different treatment devices for transferring energy to or from the airways. These are just some of the examples of the type of treatment devices which may be used to perform the methods according to the present invention. It should be recognized that each of the treatment devices described below can be modified to deliver or remove energy in different patterns depending on the treatment to be performed. The treatment devices may be actuated continuously for a predetermined period while stationary, may be pulsed, may be actuated multiple times as they are moved along an airway, may be operated continuously while moving the device in an airway to achieve a "painting" of the airway, or may be actuated in a combination of any of these techniques. The particular energy application pattern desired can be achieved by configuring the treatment device itself or by moving the treatment device to different desired treatment locations in the airway.

The treatment of an airway with the treatment device may involve placing a visualization system such as an endoscope or bronchoscope into the airways. The treatment device is then inserted through or next to the bronchoscope or endoscope while visualizing the airways. Alternatively, it is possible to build the means for visualization directly into the treatment device using fiber optic imaging and lenses or a CCD and lens arranged at the distal portion of the treatment device. The treatment device may also be positioned using radiographic visualization such as fluoroscopy or other external visualization means. The treatment device which has been positioned with a distal end within an airway to be treated is energized so that energy is applied to the tissue of the airway walls in a desired pattern and intensity. The distal end of the treatment device may be moved through the airway in a uniform painting like motion to expose the entire length of an airway to be treated to the energy. The treatment device may be passed along the airway one or more times to achieve adequate treatment. The painting like motion used to exposed the entire length of an airway to the energy may be performed by moving the entire treatment device from the proximal end either manually or by motor. Alternatively, segments, stripes, rings or other treatment patterns may be used.

According to one embodiment of the invention, the energy is transferred to or from the opening region of an airway, preferably within a length of approximately two times the airway diameter or less, and to regions of airways distal to bifurcations and side branches, preferably within a distance of approximately twice the airway diameter or less. The invention may also be used to treat long segments of un-bifurcated airway.

Figure 16:
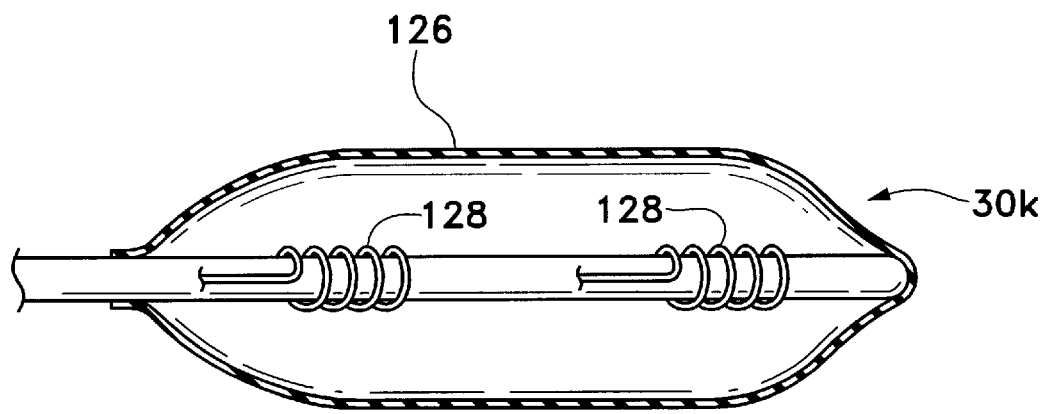
FIG. 16 is a schematic side view of a eleventh embodiment of a treatment device with a balloon for heating of tissue.
Figure 17:
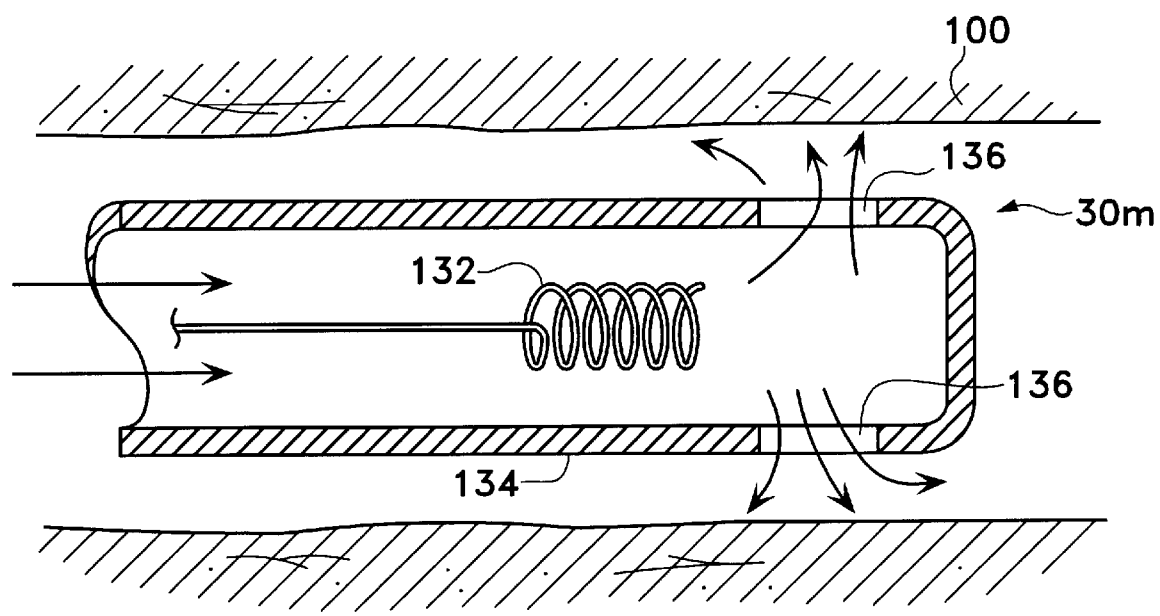
FIG. 17 is a side cross sectional view of a twelfth embodiment of a treatment device for treatment with heated fluid.
Figure 18:
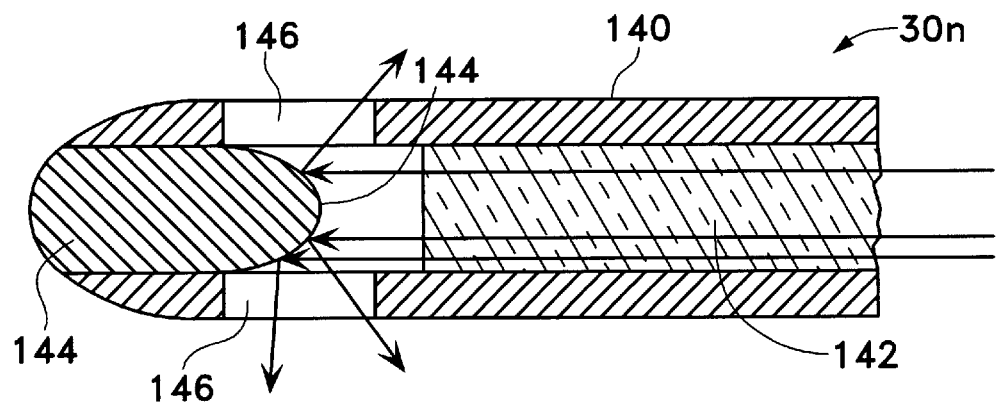
FIG. 18 is a side cross sectional view of a thirteenth embodiment of a treatment device for treatment with radiation.
Figure 19:
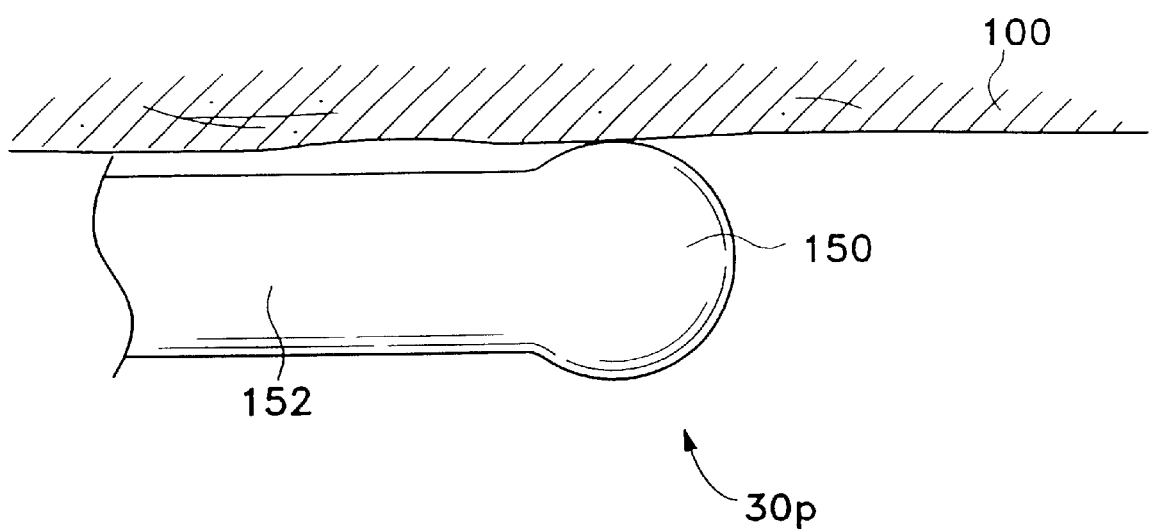
FIG. 19. is a side view of a fourteenth embodiment of a treatment device for treatment with a cryoprobe.

The treatment devices of FIGS. 5–15 include tissue contacting electrodes configured to be placed within the airway. These devices can be used for delivering radio frequency in either a monopolar or a bipolar manner or for delivering other energy to the tissue, such as conducted heat energy from resistively heated electrodes. For monopolar energy delivery, one or more electrodes of the treatment device are connected to a single pole of the energy source 32 and an optional external electrode 44 is connected to an opposite pole of the energy source. For bipolar energy delivery, multiple electrodes are connected to opposite poles of the energy source 32 and the external electrode 44 is omitted. The number and arrangement of the electrodes may vary depending on the pattern of energy delivery desired. The treatment devices of FIGS. 16–18 are used to deliver radiant or heat energy to the airway. The treatment device of FIG. 16 can also deliver indirect radio frequency or microwave energy to the tissue. Finally the treatment device of FIG. 19 is used to remove heat energy from the tissue.

Figure 5A:
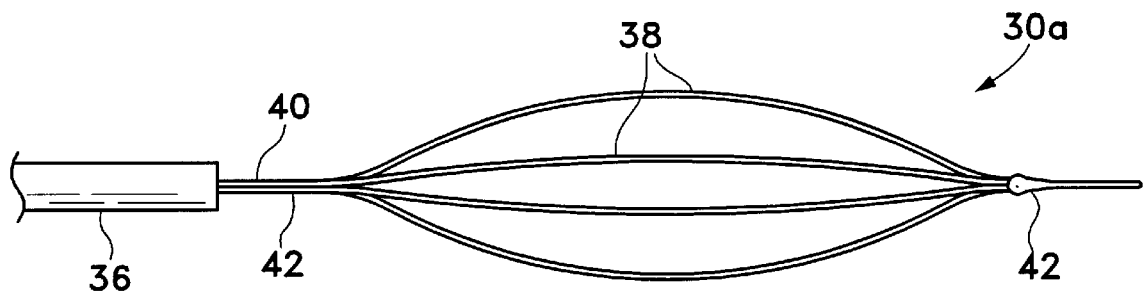
FIGS. 5A and 5B are side views of two variations of a first embodiment of a treatment device having a plurality of wire shaped electrodes.

The treatment device 30a of FIG. 5A includes a catheter 36 for delivering a shaft 40 having a plurality of electrodes 38 to a treatment site. The electrodes 38 are formed from a plurality of wires which are soldered or otherwise connected together at two connection areas 42. The electrodes 38 between the connection areas 42 are formed into a basket shape so that arch shaped portions of the wires will contact the walls of an airway. The wires may be coated with an insulating material except at the tissue contact points. Alternatively, the wires of the basket may be exposed while the connection areas 42 and shaft 40 are insulated. Preferably, the electrodes 38 are formed of a resilient material which will allow the distal end of the treatment device to be retracted into the catheter 36 for delivery of the catheter to the treatment site and will allow the electrodes to return to their original basket shape upon deployment. The treatment device 30a is preferably configured such that the electrodes 38 have sufficient resilience to come into contact with the airway walls for treatment.

Figure 5B:
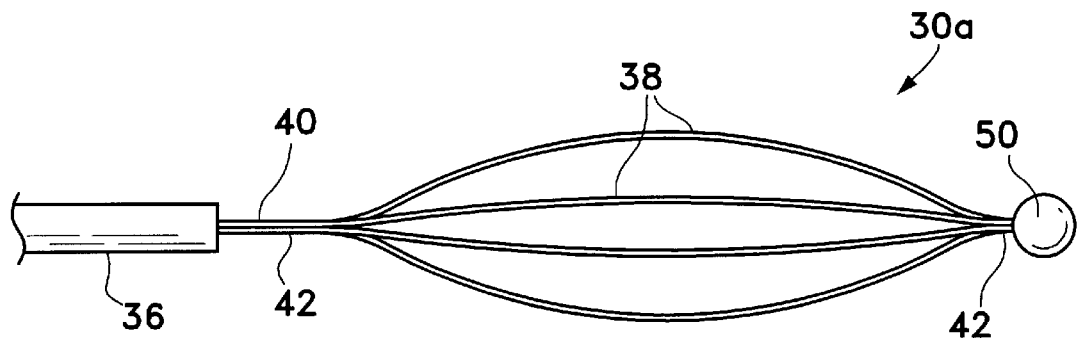
Figure 5C:
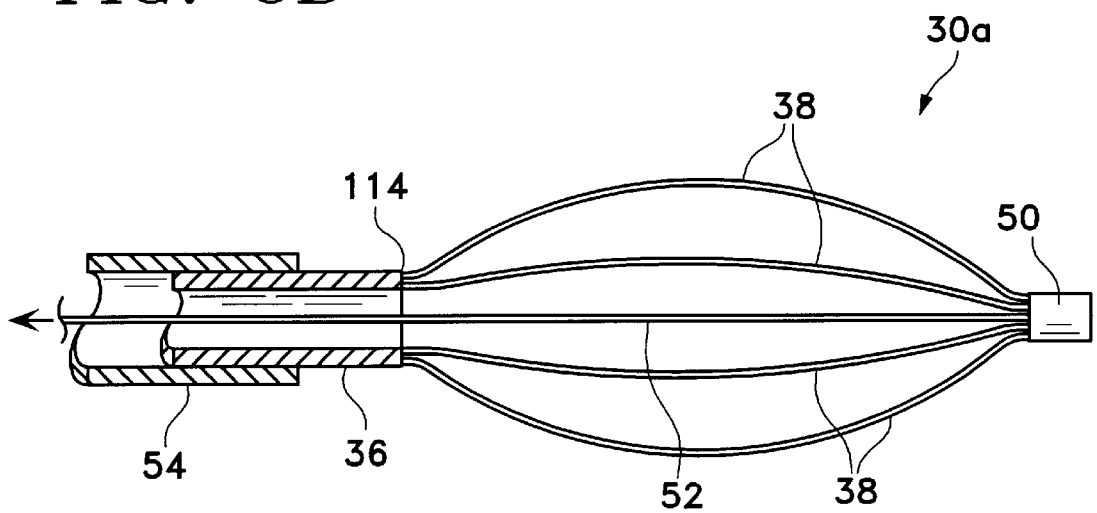
FIG. 5C is a cross sectional side view of another variation of the first embodiment of a treatment device having a plurality of wire shaped electrodes.

FIG. 5B illustrates the treatment device 30a in which the distal end of the device is provided with a ball shaped member 50 for easily inserting the device to a treatment site without causing trauma to surrounding tissue. FIG. 5C illustrates the treatment device 30a having electrodes 38 connected to the distal end of the catheter 36 and forming a basket shape. The basket shape may be expanded radially during use to insure contact between the electrodes 38 and the airway walls by pulling on a center pull wire 52 which is connected to a distal end 50 of the device and extends through a lumen of the catheter 36. The treatment device 30a may be delivered to a treatment site through a delivery catheter or sheath 54 and may be drawn along the airway to treat the airway in a pattern of longitudinal or helical stripes.

Figure 6:
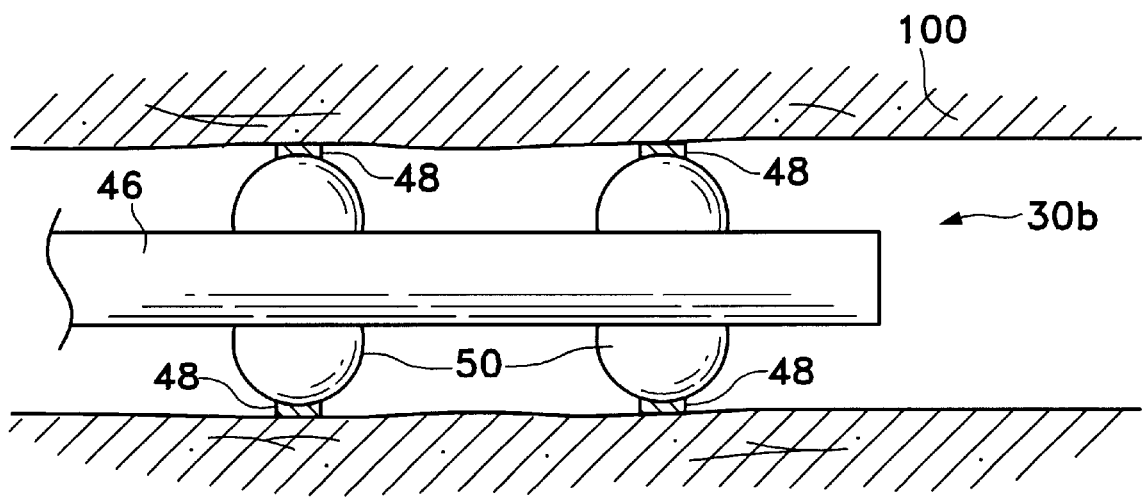
FIG. 6 is a side view of a second embodiment of a treatment device with electrodes positioned on expandable balloons.

FIG. 6 illustrates a treatment device 30b in which a catheter shaft 46 is provided with a plurality of electrodes 48 positioned on inflatable balloons 50. The balloons 50 are inflated through the catheter shaft 46 to cause the electrodes 48 come into contact with the airway walls 100. The electrodes 48 are preferably connected to the energy source 32 by conductive wires (not shown) which extend from the electrodes through or along the balloons 50 and through the catheter shaft 46 to the energy source. The electrodes may be used in a bipolar mode without an external electrode. Alternatively, the treatment device 30*b* may be operated in a monopolar mode with an external electrode 44. The electrodes 48 may be continuous circular electrodes or may be spaced around the balloons 50.

Figure 7:
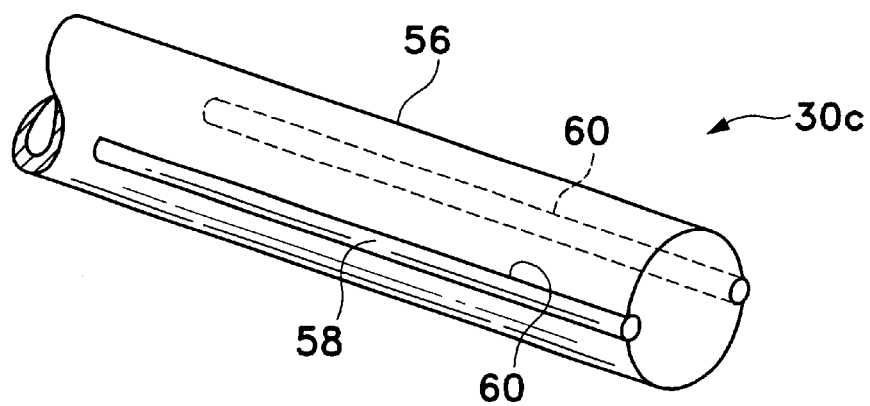
FIG. 7 is a perspective view of a third embodiment of a treatment device with electrodes positioned in grooves.

An alternative treatment device 30*c* of FIG. 7 includes a catheter 56 having one or more grooves 60 in an exterior surface. Positioned within the grooves 60 are electrodes 58 for delivery of energy to the airway walls. Although the grooves 60 have been illustrated in a longitudinal pattern, the grooves may be easily configured in any desired pattern. Preferably, the treatment device 30*c* of FIG. 7 includes a biasing member (not shown) for biasing the catheter 56 against the airway wall such that the electrodes 58 contact the tissue. The biasing member may be a spring element, an inflatable balloon element, or other biasing member. Alternatively, the biasing function may be performed by providing a preformed curve in the catheter 56 which causes the catheter to curve into contact with the airway wall when extended from a delivery catheter.

Figure 8:
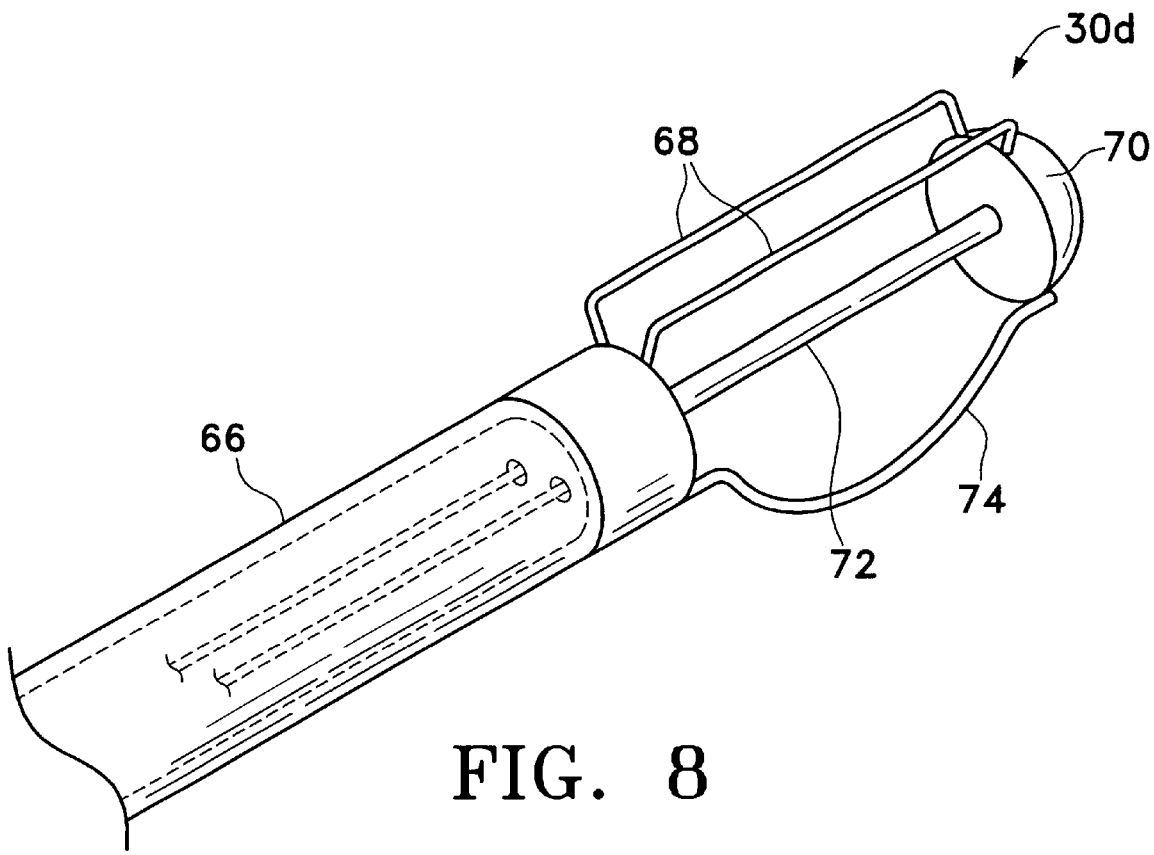
FIG. 8 is a perspective view of a fourth embodiment of a treatment device with electrodes and a biasing element.

FIG. 8 illustrates a treatment device 30*d* having one or more electrodes 68 connected to a distal end of a catheter 66. The electrodes 68 are supported between the distal end of the catheter 66 and a device tip 70. A connecting shaft 72 supports the tip 70. Also connected between the distal end of the catheter 66 and the tip 70 is a spring element 74 for biasing the electrodes 68 against a wall of the airway. The spring element 74 may have one end which slides in a track or groove in the catheter 66 such that the spring can flex to a variety of different positions depending on an internal diameter of the airway to be treated.

Figure 9:
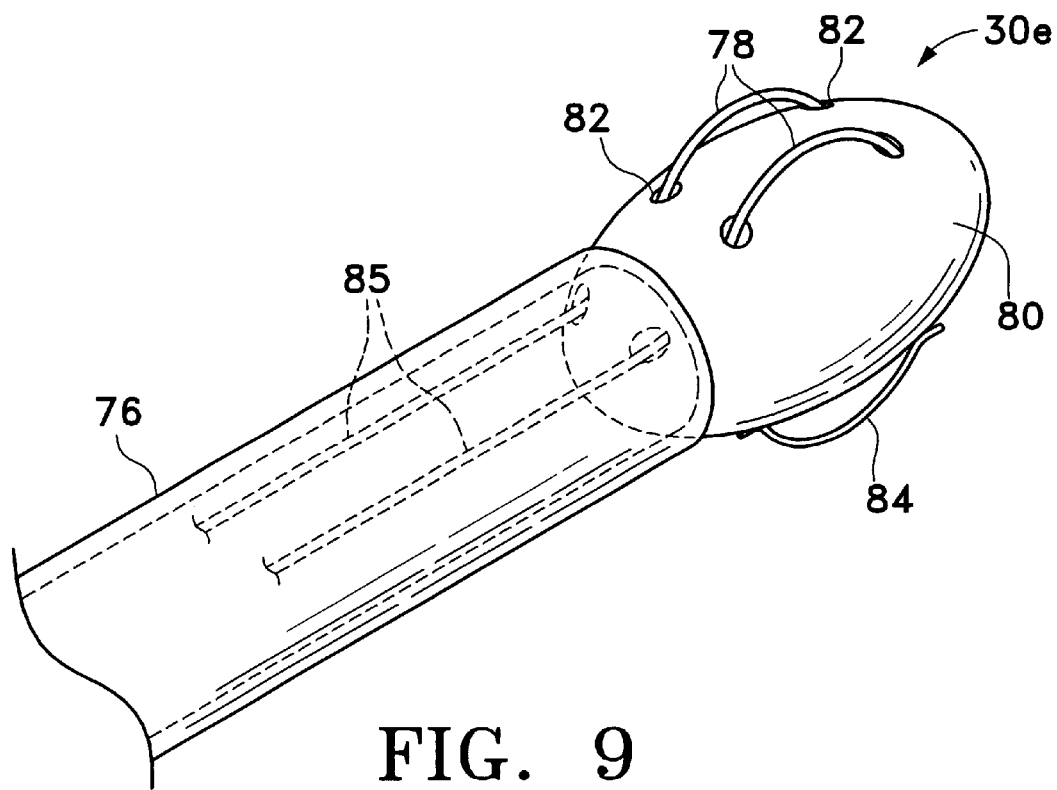
FIG. 9 is a perspective view of a fifth embodiment of a treatment device with electrodes and a biasing element.

FIG. 9 illustrates an alternative treatment device 30*e* in which the one or more electrodes 78 are positioned on a body 80 secured to an end of a catheter 76. In the FIG. 9 embodiment, the body 80 is illustrated as egg shaped, however, other body shapes may also be used. The electrodes 78 extend through holes 82 in the body 80 and along the body surface. A biasing member such as the spring element 84 is preferably provided on the body 80 for biasing the body with the electrodes against the airway walls. Leads 85 are connected to the electrodes and extend through the catheter 76 to the energy source 32.

Figure 10:
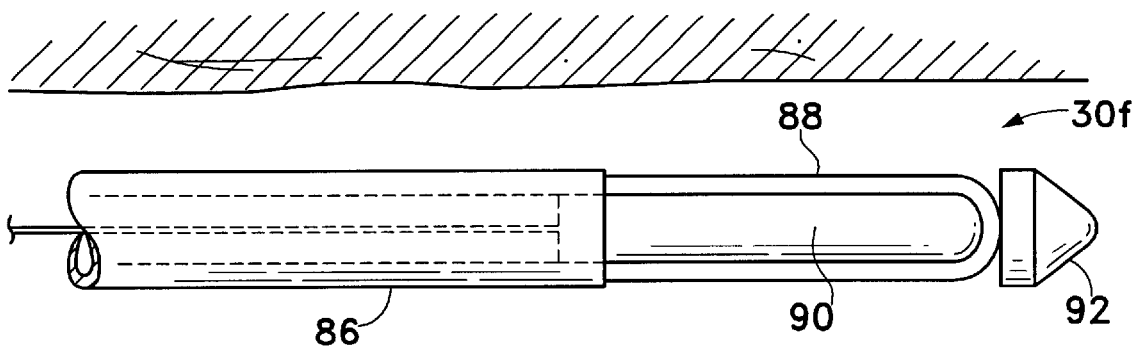
FIG. 10 is a side view of a sixth embodiment of a treatment device in an unexpanded position.
Figure 11:
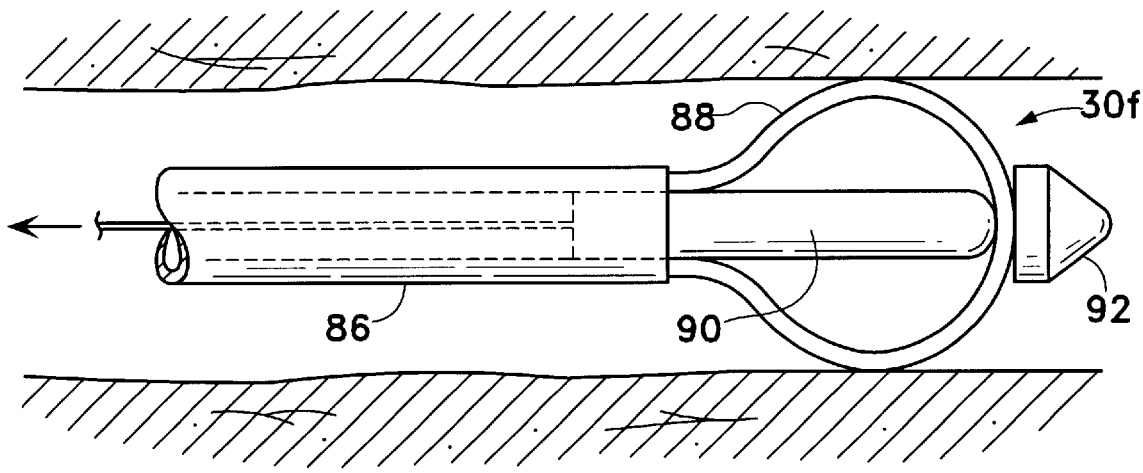
FIG. 11 is a side view of the treatment device of FIG. 10 in an expanded position.

FIGS. 10 and 11 illustrate a further treatment device 30*f* having one or more loop shaped electrodes 88 connected to a catheter shaft 86. In the unexpanded position shown in FIG. 10, the loop of the electrode 88 lies along the sides of a central core 90. A distal end of the loop electrode 88 is secured to the core 90 and to an optional tip member 92. The core 90 is slidable in a lumen of the catheter 86. Once the treatment device 30*f* has been positioned with the distal end in the airway to be treated, the electrode is expanded by pulling the core 90 proximally with respect to the catheter 86, as shown in FIG. 11. Alternatively, the electrode 88 or the core 90 may be spring biased to return to the configuration of FIG. 11 when a constraining force is removed. This constraining force may be applied by a delivery catheter or bronchoscope through which the treatment device 30*f* is inserted or by a releasable catch.

Figure 12:
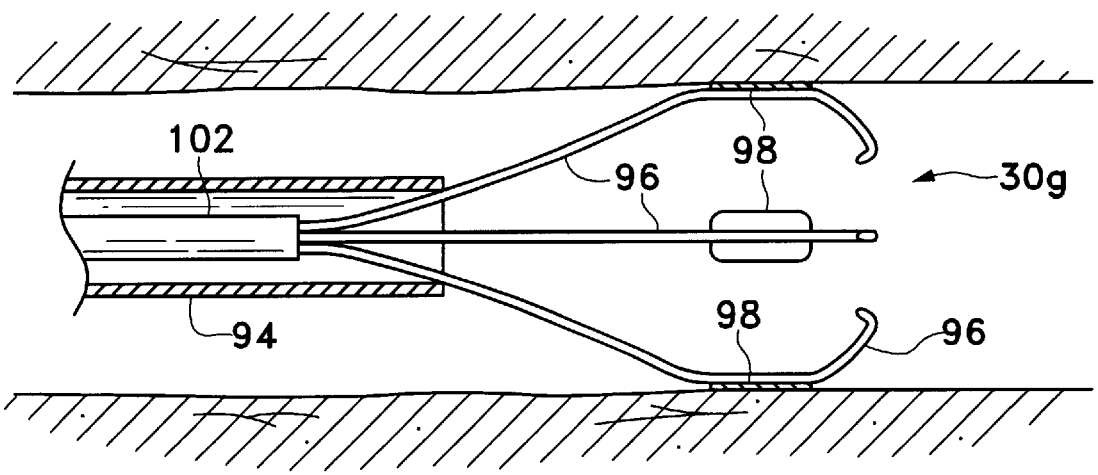
FIG. 12 is a side view of a seventh embodiment of a treatment device in an expanded position.

The treatment device 30*g* of FIG. 12 includes a plurality electrodes 98 positioned on leaf springs 96 which are outwardly biased. The leaf springs 96 are connected to a shaft 102 which is positioned within a delivery catheter 94. The leaf springs 96 and electrodes 98 are delivered through the delivery catheter 94 to a treatment site within the airways. When the leaf springs 96 exit the distal end of the delivery catheter 94, the leaf springs bend outward until the electrodes 98 come into contact with the airway walls for application of energy to the airway walls.

Figure 13:
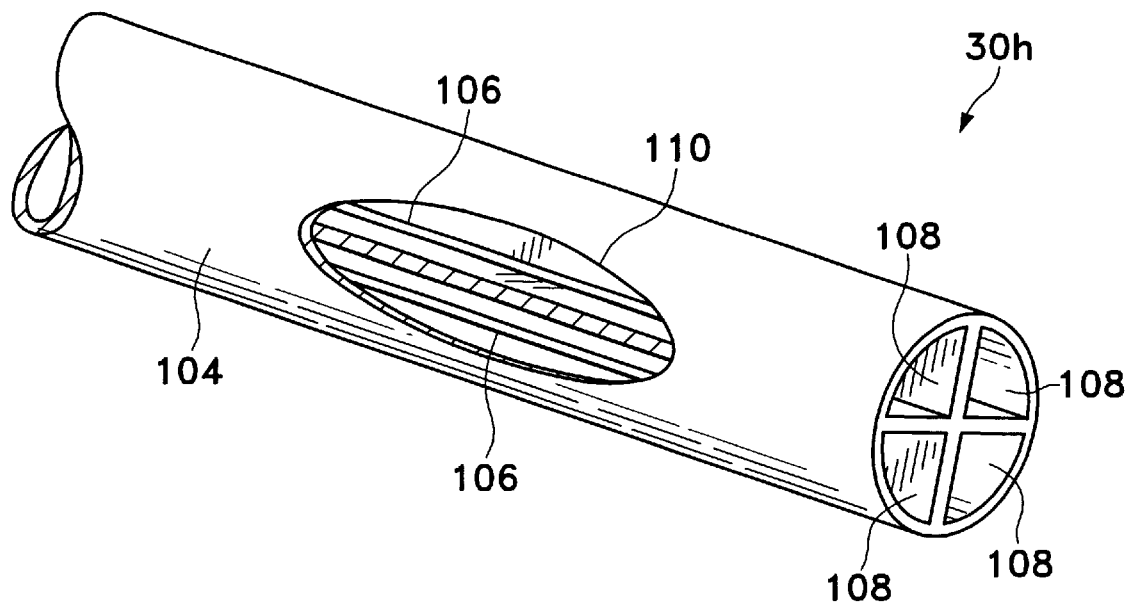
FIG. 13 is a side view of an eighth embodiment of a treatment device having a plurality of lumens containing electrodes.
Figure 14:
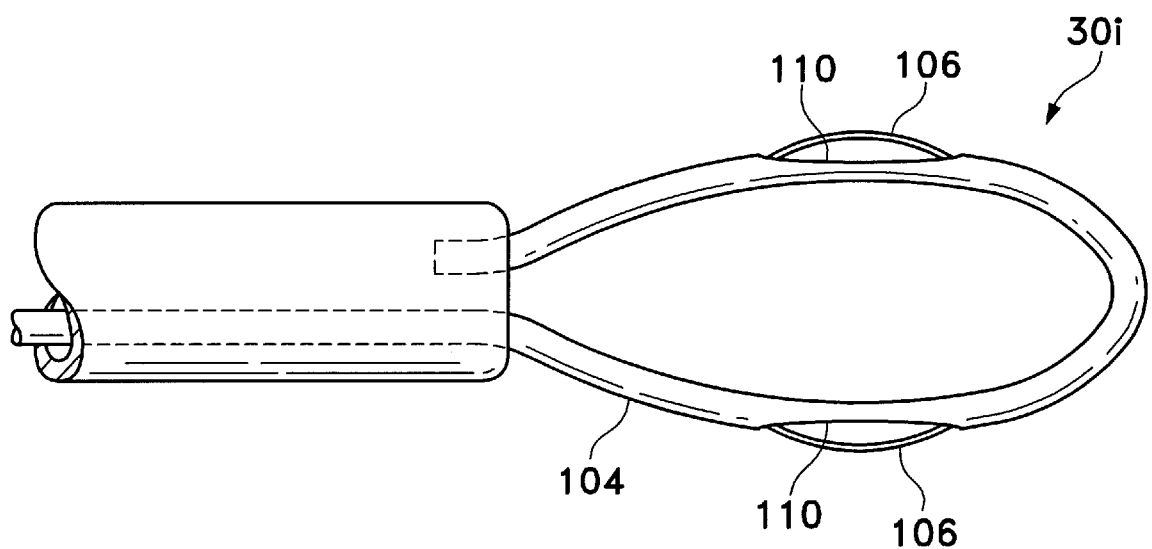
FIG. 14 is a side view of a ninth embodiment of a treatment device having electrodes exposed by cut away sections of a tube.

FIGS. 13 and 14 illustrate embodiments of treatment devices 30*h*, 30*i* in which electrodes 106 in the form of wires are positioned in one or more lumens 108 of a catheter 104. Openings 110 are formed in the side walls of the catheters 104 to expose the electrodes 106. As shown in FIG. 13, the treatment device 30*h* has multiple lumens 108 with electrodes provided in each of the lumens. The side wall of the treatment device 30*h* is cut away to expose one or more of the electrodes 106 through a side wall opening 110. In FIG. 13, the opening 110 exposes two electrodes positioned in adjacent lumens. The treatment device 30*h* may be provided with a biasing member as discussed above to bring the electrodes 106 of the device into contact with the airway wall.

The treatment device 30*i* of FIG. 14 includes a catheter 104 which has been formed into a loop shape to allow the electrode 106 to be exposed on opposite sides of the device which contact opposite sides of the airway. The resilience of the loop shape causes the electrodes to come into contact with the airway walls.

Figure 15:
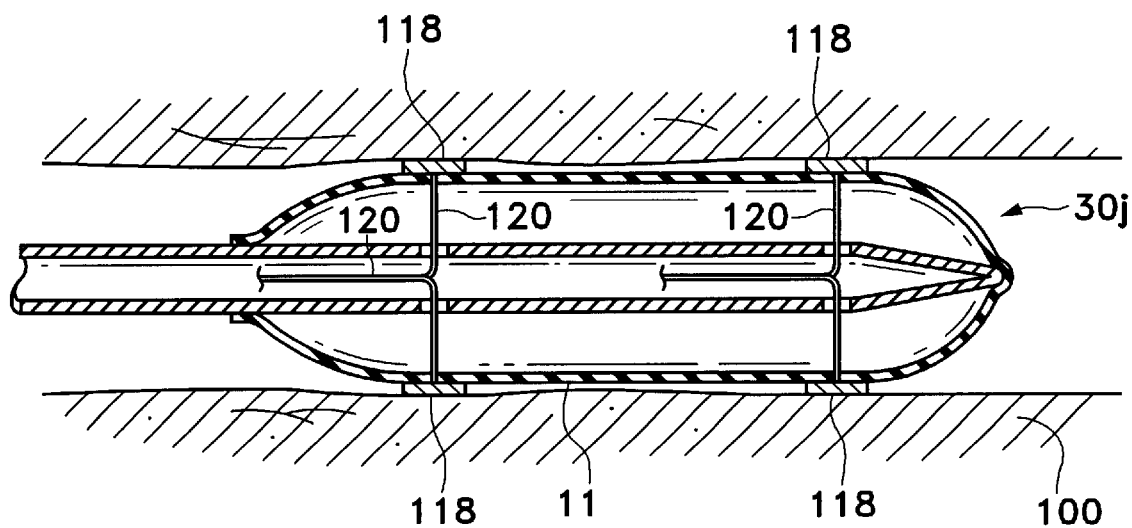
FIG. 15 is a side cross sectional view of a tenth embodiment of a treatment device with electrodes positioned on an expandable balloon.

The treatment device 30*j* of FIG. 15 is in the form of a balloon catheter. The treatment device 30*j* includes electrodes 118 positioned on an exterior surface of an inflatable balloon 116. The electrodes 118 are electrically connected to the energy source 32 by the leads 120 extending through the balloon and through the lumen of the balloon catheter 114. The balloon 116 is filled with a fluid such as saline or air to bring the electrodes into contact with the airway wall 100.

FIG. 16 shows an alternative embodiment of a balloon catheter treatment device 30*k* in which a fluid within the balloon 126 is heated by internal electrodes 128. The electrodes 128 are illustrated in the shape of coils surrounding the shaft of the catheter 124, however other electrode shapes may also be used. The electrodes 128 may be used as resistance heaters by application of an electric current to the electrodes. Alternatively, radio frequency or microwave energy may be applied to the electrodes 128 to heat a fluid within the balloon 126. The heat then passes from an exterior of the balloon 126 to the airway wall. The radio frequency or microwave energy may also be applied indirectly to the airway wall through the fluid and the balloon. In addition, hot fluid may be transmitted to the balloon 126 from an external heating device for conductive heating of the airway tissue.

FIG. 17 illustrates a treatment device 30*m* for delivering heated fluid to the airway walls to heat the airway tissue. The device 30*m* includes a heating element 132 provided within a fluid delivery catheter 134. The fluid passes over the heating element 132 and out of openings 136 in the end of the catheter 134. The openings 136 are arranged to direct the fluid at the airway walls 100. The heating element 132 may be a coiled resistance heating element or any other heating element. The heating element 132 may be positioned anywhere along the body of the catheter 134 or may be an external heating device separate from the catheter.

The heating element 132 may also be replaced with a friction producing heating element which heats fluid passing through the fluid delivery catheter 134. According to one embodiment of a friction producing heating element, a friction element rotates and contacts a stationary element for purposed of heating the fluid.

FIG. 18 illustrates a treatment device 30n for delivery of light or other radiant energy to the walls of the airway. The light delivery device 30n includes an outer catheter or sheath 140 surrounding a light transmitting fiber 142. A light directing member 144 is positioned at a distal end of the light delivery device for directing the light to the airway walls. The sheath 140 includes a plurality of windows 146 which allow the light which has been redirected by the light directing member 144 to pass substantially radially out of the sheath. The light delivery device 30n is connected by a conventional optical connection to a light source 32.

The light used may be coherent or incoherent light in the range of infrared, visible, or ultraviolet. The light source 32 may be any known source, such as a UV laser source. The light source 32 may be an ultraviolet light source having a wavelength of about 180–308 nm, a visible light source, or an infrared light source preferably in the range of 800–2200 nm. The intensity of the light may vary depending on the application. The light intensity should be bright enough to penetrate any mucus present in the airway and penetrate the airway walls to a depth necessary to treat the selected tissue. The light intensity may vary depending on the wavelength used, the application, the thickness of the smooth muscle, and other factors. The light or other radiant energy may also be used to heat an absorptive material on the catheter or sheath which in turn conductively heats the airway wall.

U.S. application Ser. No. 09/095,323 filed Jun. 10, 1998, illustrates different exemplary embodiments of the distal tip of the light delivery device 34n for irradiating the airway walls.

FIG. 19 shows an alternative embodiment of a treatment device 30p including a cryoprobe tip 150 for transferring or removing energy in the from of heat from an airway wall 100. The cryoprobe tip 150 is delivered to the treatment site by a cryoprobe shaft 152. Transfer of energy from the tissue structures of the airway wall can be used in the same manner as the delivery of energy with any of the devices discussed above. The particular configuration of the cryoprobe treatment device 30p may vary as is known in the art.

The treatment of the tissue in the airway walls by transfer of energy according to the present invention provides improved long term relief from asthma symptoms for some asthma sufferers. However, over time, some amount of smooth muscle or mucus gland cells which were not affected by an initial treatment may regenerate and treatment may have to be repeated after a period of time such as one or more months or years.

The airways which are treated with the methods according to the present invention are preferably 1 mm in diameter or greater, more preferably 3 mm in diameter or greater. The methods are preferably used to treat airways of the second to eighth generation, more preferably airways of the second to sixth generation.

Although the present invention has been described in detail with respect to methods for the treatment of airways in the lungs, it should be understood that the present invention may also be used for treatment of other body conduits. For example, the treatment system may be used for reducing smooth muscle and spasms of the esophagus of patients with achalasia or esophageal spasm, in coronary arteries of patients with Printzmetal's angina variant, for ureteral spasm, for urethral spasm, and irritable bowel disorders.

The methods according to the present invention provide a more effective and/or permanent treatment for asthma than the currently used bronchodilating drugs, drugs for reducing mucus secretion, and drugs for decreasing inflammation.

While the invention has been described in detail with reference to the preferred embodiments thereof, it will be apparent to one skilled in the art that various changes and modifications can be made and equivalents employed, without departing from the present invention.

What is claimed is:

1. A method for treating conditions of the lungs by decreasing airway responsiveness comprising:

transferring energy to or from an airway wall in the lungs to alter the airway wall in such a manner that the responsiveness of the airway is reduced.

2. The method of claim 1, wherein the energy transfer alters the structure of the airway wall.

3. The method of claim 1, wherein the energy transfer alters the function of the airway wall.

4. The method of claim 1, wherein the method is used to treat asthma by preventing contraction of the airway.

5. The method of claim 1, wherein the energy transfer alters the airway in such a manner that the ability of the airway to narrow is impaired.

6. The method of claim 1, wherein the energy is transferred to the airway by moving an energy transfer device along the airway.

7. The method of claim 1, wherein the energy is transferred to a portion of the airway by an energy transfer device which creates one or more energy transfer patterns.

8. The method of claim 7, wherein the energy transfer pattern is a pattern of one or more spots having a rectangular, elliptical, circular, or other shape.

9. The method of claim 7, wherein the energy is transferred to the airway in a band pattern covering a full diameter of the airway.

10. The method of claim 7, wherein the energy is transferred to the airway in a pattern of at least one stripe extending along the airway in a longitudinal or helical pattern.

11. The method of claim 1, wherein the energy is transferred to the airway at the location of an opening of an airway, a bifurcation, or an opening of a side branch.

12. The method of claim 1, wherein the energy is transferred to the airway at a segment of the airway between bifurcations, openings, or side branches.

13. The method of claim 1, wherein the energy is transferred to the airway by activating an energy transfer device, deactivating the energy transfer device, moving the energy transfer device, and reactivating the energy transfer device.

14. The method of claim 1, wherein the energy transfer alters smooth muscle of the airway wall in such a manner that the responsiveness of the airway is reduced.

15. The method of claim 14, wherein the ability of the smooth muscle to contract is altered.

16. The method of claim 15, wherein shortening of all or some of the smooth muscle is reduced or prevented.

17. The method of claim 14, wherein the energy transfer alters a connection between the smooth muscle and the airway wall.

18. The method of claim 14, wherein the energy transfer eliminates at least a portion of the smooth muscle.

19. The method of claim 14, wherein the energy transfer prevents the smooth muscle from replicating.

20. The method of claim 1, wherein the energy transfer alters mucus producing cells or glands in the airway wall in such a manner that the responsiveness of the airway is reduced.

21. The method of claim 20, wherein the energy transfer eliminates at least a portion of the mucus producing cells or glands.

22. The method of claim 20, wherein the energy transfer prevents the mucus producing cells or glands from replicating.

23. The method of claim 20, wherein the energy transfer alters the ability of the mucus producing cells or glands to produce or secrete mucus.

24. The method of claim 1, wherein the energy transfer alters production or release of inflammatory mediators in at least a part of the airway.

25. The method of claim 24, wherein the energy transfer prevents replication of structures producing or releasing inflammatory mediators.

26. The method of claim 24, wherein the energy transfer eliminates at least a portion of the structures which produce or release inflammatory mediators.

27. The method of claim 24, wherein the energy transfer alters the ability of structures in the airway to produce or release inflammatory mediators.

28. The method of claim 1, wherein the energy transfer increases resistance to airway caliber reduction in at least a part of the airway.

29. The method of claim 28, wherein the increased resistance is produced by thickening or fibrosing the airway wall.

30. The method of claim 28, wherein the increased resistance is produced by increasing parenchymal tethering.

31. The method of claim 28, wherein the increased resistance is produced by increasing connection support between the airway and support structures.

32. The method of claim 1, wherein the energy transfer alters at least a part of the epithelium in the airway wall.

33. The method of claim 32, wherein the energy transfer eliminates epithelium.

34. The method of claim 32, wherein the energy transfer stimulates healing of the epithelium.

35. The method of claim 32, wherein the energy transfer stimulates replacement of the epithelium.

36. The method of claim 1, wherein the energy transfer alters at least a part of a submucosal layer in the airway wall.

37. The method of claim 36, wherein the energy transfer reduces a thickness of the submucosal layer.

38. The method of claim 1, wherein the energy transfer alters mucosal folding.

39. The method of claim 38, wherein the structure of the airway wall is altered by increasing a number of mucosal folds or decreasing a size of mucosal folds.

40. The method of claim 1, wherein a photodynamic agent is delivered to the airway wall and the energy transfer stimulates the photodynamic agent.

41. The method of claim 1, wherein the airways treated are at least 1 mm in diameter.

42. The method of claim 41, wherein the airways treated are at least 3 mm in diameter.

43. The method of claim 1, wherein the airways treated are generations 2 through 8.

44. The method of claim 43, wherein the airways treated are generations 2 through 6.

45. The method of claim 1, wherein the airway treated are visualizable with a bronchoscope.

46. A method for treating conditions of the lungs by decreasing airway resistance to airflow comprising:
    transferring energy to or from an airway wall in the lungs to alter the airway wall in such a manner that a resistance to airflow of the airway is decreased.

47. The method of claim 46, wherein the energy transfer alters a structure of the airway wall to increase an effective caliber of the airway.

48. The method of claim 47, wherein the structure of the airway wall is altered by decreasing a thickness of the airway wall.

49. The method of claim 46, wherein the energy transfer alters a function of the airway wall to increase an effective caliber of the airway.

50. The method of claim 49, wherein the function of the airway wall is altered by reducing mucus or mucus plugging.

51. The method of claim 49, wherein the function of the airway is altered by reducing tissue inflammation.

52. The method of claim 51, wherein inflammation is reduced by reducing edema or healing epithelium.

53. The method of claim 49, wherein the function of the airway wall is altered by altering a resting tone of the airway wall.

54. The method of claim 53, wherein the resting tone is altered by altering the smooth muscle or by denervation.

* * * * *

UNITED STATES PATENT AND TRADEMARK OFFICE
CERTIFICATE OF CORRECTION

PATENT NO.    : 6,411,852 B1
DATED         : June 25, 2002
INVENTOR(S)   : Christopher J. Danek et al.

It is certified that error appears in the above-identified patent and that said Letters Patent is hereby corrected as shown below:

<u>Title page,</u>
Item [75], Inventors, please add -- Michael D. Laufer, Menlo Park, California --.

Signed and Sealed this

Thirteenth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO.        : 6,411,852 B1                                        Page 1 of 1
APPLICATION NO.   : 09/296040
DATED             : June 25, 2002
INVENTOR(S)       : Christopher J. Danek et al.

It is certified that error appears in the above-identified patent and that said Letters Patent is hereby corrected as shown below:

Title page, Item (63), please replace:
"Continuation-in-part of application No. 09/095,323, filed on Jun. 10, 1998." with:
-- Continuation-in-part of application No. 09/095,323, filed on Jun. 10, 1998, continuation-in-part of application No. 08/994,064, filed on Dec. 19, 1997, now Pat. No. 6,083,255, continuation-in-part of application No. 09/224,937, filed on December 31, 1998, now Pat. No. 6,200,333, and a continuation-in-part of application No. 09/260,401, filed on Mar. 1, 1999, now Pat No. 6,283,988, which is a continuation-in-part of application No. 09/003,750, filed on Jan. 7, 1998, now Pat. No, 5,972,026, which is a continuation-in-part of application No. 08/833,550, filed on Apr. 7, 1997, now Pat. No. 6,273,907.--; and In column 1, lines 4-6, please replace:
"This is a Continuation-in-part application of U.S. application Ser. No. 09/095,323 filed Jun. 10, 1998, which is incorporated herein by reference in its entirety." with:
-- This is a Continuation-in-part application of U.S. application Ser. No. 09/095,323 filed Jun. 10, 1998, which is incorporated herein by reference in its entirety, and is a Continuation-in-part application of U.S. application Ser. No. 08/994,064 filed Dec. 19, 1997, now U.S. Pat. No. 6,083,255, and is a Continuation-in-part application of U.S. application Ser. No. 09/224,937 filed December 31, 1998, now U.S. Pat. No. 6,200,333, and is a Continuation-in-part application of U.S. application Ser. No. 09/260,401 filed Mar. 1, 1999, now U.S. Pat. No. 6,283,988, which is a Continuation-in-part application of U.S. application Ser. No. 09/003,750 filed Jan. 7, 1998, now U.S. Pat. No. 5,972,026, which is a Continuation-in-part application of U.S. application Ser. No.08/833,550 filed Apr. 7, 1997, now U.S. Pat. No. 6,273,907.--

Signed and Sealed this

Thirteenth Day of November, 2007

JON W. DUDAS
*Director of the United States Patent and Trademark Office*